(12) United States Patent
Biberger (10) Patent No.: US 8,007,718 B1
(45) Date of Patent: Aug. 30, 2011

(54) SYSTEM FOR AND METHOD OF PROCESSING BONE MATERIAL USING SUPERCRITICAL FLUIDS

(75) Inventor: Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

(21) Appl. No.: 12/151,840

(22) Filed: May 8, 2008

Related U.S. Application Data (60) Provisional application No. 60/928,946, filed on May 11, 2007.

(51) Int. Cl.
| | |
|---|---|
| A61L 9/00 | (2006.01) |
| A61L 2/00 | (2006.01) |
| C07G 15/00 | (2006.01) |
| A61F 2/02 | (2006.01) |
| A61F 2/28 | (2006.01) |
| C03C 23/00 | (2006.01) |
| B08B 5/04 | (2006.01) |
| B08B 5/00 | (2006.01) |
| A01N 63/00 | (2006.01) |
| A61K 39/00 | (2006.01) |
| C12N 1/00 | (2006.01) |
| A23J 1/00 | (2006.01) |

(52) U.S. Cl. ............... 422/28; 422/1; 422/31; 422/32; 422/33; 422/292; 422/295; 435/268; 435/235.1; 435/243; 435/255.1; 623/16; 623/11; 623/66; 623/920; 623/923; 134/1; 134/2; 134/21; 134/31; 134/33; 134/30; 134/26; 424/184.1; 424/93.1; 530/422

(58) Field of Classification Search ............... 422/1, 28, 422/31–33, 292, 295; 435/268, 235.1, 243, 435/255.1; 623/16, 11, 66, 920, 923; 134/1–2, 134/21, 31, 33, 30, 26; 424/184.1, 93.1; 530/422

See application file for complete search history.

(56) References Cited

U.S. PATENT DOCUMENTS

| | | | | |
|---|---|---|---|---|
| 5,725,579 | A | * | 3/1998 | Fages et al. ............... 128/898 |
| 2003/0066800 | A1 | | 4/2003 | Saim et al. |
| 2003/0072677 | A1 | * | 4/2003 | Kafesjian et al. ............ 422/33 |
| 2004/0023453 | A1 | | 2/2004 | Xu et al. |
| 2004/0064964 | A1 | * | 4/2004 | Lee ............................ 34/343 |
| 2007/0173403 | A1 | | 7/2007 | Koike et al. |

OTHER PUBLICATIONS

Office Action dated May 4, 2009, U.S. Appl. No. 12/151,932, filed May 8, 2008.

* cited by examiner

*Primary Examiner* — Jill Warden
*Assistant Examiner* — Monzer R Chorbaji
(74) *Attorney, Agent, or Firm* — Haverstock & Owens LLP (57) ABSTRACT

A method of processing bone material using supercritical fluids is disclosed. The method comprises placing the bone material in a processing chamber, adding supercritical fluid to the processing chamber, pulsing the supercritical fluid in the processing chamber, and rinsing the bone material. A processing system for processing bone material using supercritical fluids in accordance with the present invention comprises a processing chamber for housing the bone material, a vat for storing a processing fluid, a pump, a heating element, a flow path, a tank, and a solvent port.

19 Claims, 5 Drawing Sheets

SYSTEM FOR AND METHOD OF PROCESSING BONE MATERIAL USING SUPERCRITICAL FLUIDS

RELATED APPLICATIONS

This application claims priority under 35 U.S.C. §119(e) to Provisional U.S. Patent Application No. 60/928,946 filed May 11, 2007 entitled "MATERIAL PRODUCTION SYSTEM AND METHOD" which are hereby incorporated by reference.

FIELD OF THE INVENTION

The present invention relates generally to the field of processing organic donor material. More specifically, the present invention relates to a system for and a method of processing bone material using supercritical fluids.

BACKGROUND OF THE DISCLOSURE

The treating and processing of bone material is becoming increasingly important as the demand for bone implants and grafts (hereinafter "bone grafts" or "grafts") rises. Bone material must be processed properly; otherwise, disastrous consequences may result from implants of improperly processed bone material into a host. Such disastrous consequences include but are not limited to: a host's immunogenic response to the graft, a host's rejection of the bone graft altogether, the possible transfer of diseases and infectious agents from the donor to the host due to unclear bone grafts, prolonged recovery time for the host, and multiple avoidable operations on the host to remove an improperly processed bone graft. To avoid such problems, bone material must be properly processed to selectively eliminate fats, proteins, donor cells, viruses, bacteria, and the like, before the bone material can be successfully implanted into the host.

Figure 1:
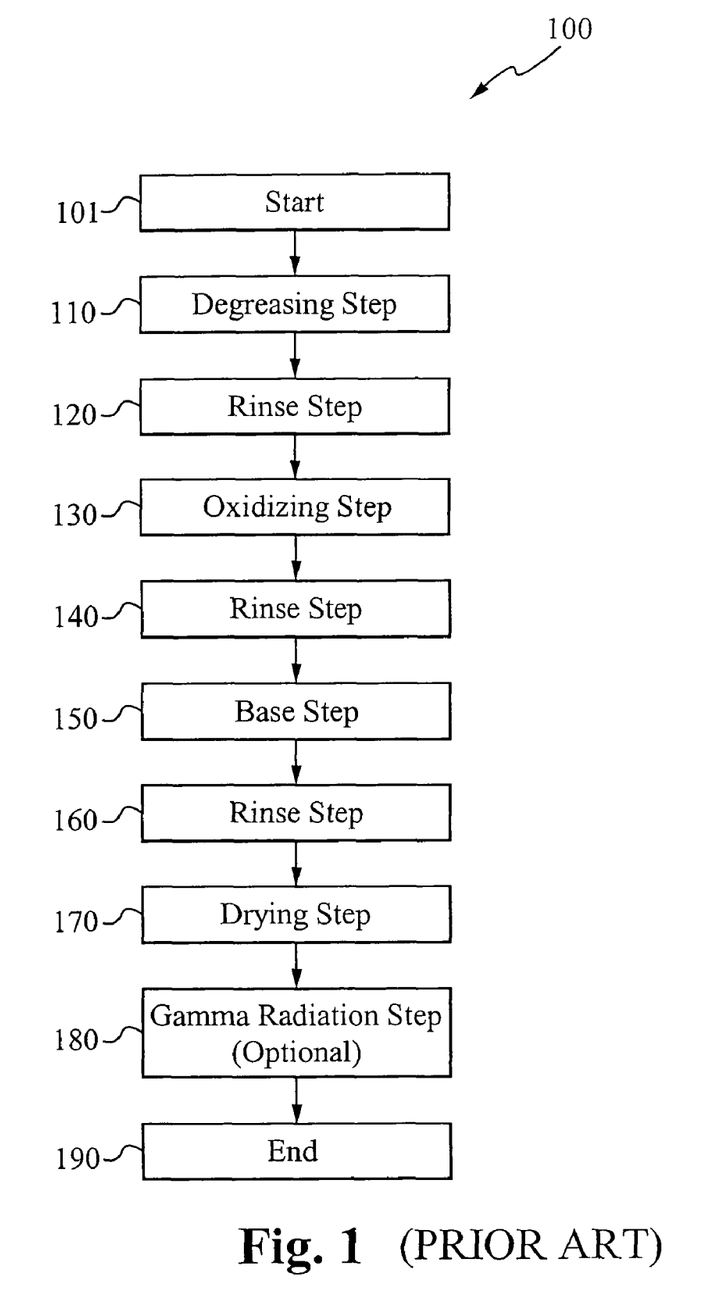
FIG. 1 is a flow chart illustrating the conventional sequence of steps for processing bone material.

Conventionally, the processing of bone material includes a number of steps. FIG. 1 shows a flow chart 100 of the steps using the conventional method of processing bone material as disclosed in the prior art. In the step 101, the bone material is obtained from a donor. In the step 110, the bone material is degreased by placing it into a container of acid or acetone. In the step 120, the bone material is rinsed using a rinse medium, such as a water bath. Next, in the step 130 the bone material is oxidized, where the bone material is sterilized from viruses and the like. Usually, this oxidizing step requires the bone to be treated with hydrogen peroxide. In the step 140 the bone material is rinsed again. In the step 150, the bone material is treated with a base for protein removal. In the step 160, the bone material undergoes yet another rinse. Then, in the step 170, the bone material is dried using some type of alcohol or acetone. Optionally, in the step 180, the bone material is treated with gamma radiation. In the step 190, the final product resulting from the conventional method is a white, bleached sterile demineralized bone matrix, which oftentimes has denatured collagen and lacks bone morphogenic proteins (BMPs), which are growth factors key to bone osteoconductivity and osteoinductivity.

The conventional method falls short in providing the ideal bone graft. The ideal bone graft is one that is both osteoconductive and osteoinductive. Osteoconductivity and osteoinductivity are two vital mechanisms for the regeneration and rebuilding of bone. Osteoinductivity refers to the ability to build, heal and regenerate bone in humans, and this is realized through active recruitment of host stem cells from surrounding tissue, which differentiate into bone-forming osteoblasts. Growth factors, particularly BMPs, aid and stimulate bone osteoinductivity. Collagen found inside the bone material provides an exceptional osteoinductive substrate for bone formation. To be osteoinductive, the ideal bone graft must contain undamaged BMPs and collagen. In contrast with osteoinductivity, osteoconductivity refers to the ability of a bone graft to form a scaffold or a structure on which the host's cells are able to form new bone. Thus, the ideal bone graft is both osteoinductive and osteoconductive, since such a graft allows for new bone to form at the implant site and further provides structural support for the formation and incorporation of the new bone.

The disadvantages of the conventional method are several-fold. First, the conventional method requires several separate processing chambers for the bone material to be processed, using a multitude of chemicals, some of which are toxic. For instance, acetone can be used for the degreasing step, step 110, and the drying step, step 170, of the conventional method, and yet in some countries, acetone is a prohibited processing agent due to its toxicity. Second, the conventional method can be expensive, labor-intensive, and time-consuming, given the numerous steps and various processing agents that are required. Also, the number of steps required by the conventional method increases the likelihood that some type of error will occur and the bone material will be improperly processed. Further, the oxidizing step, step 130, of the conventional method destroys the BMPs in the bone, leaving a sterile mineral matrix. Finally, the base step of the conventional method, step 150, can denature collagen and destroy BMPs. By denaturing collagen and killing growth factors, such as the BMPs, the conventional method unfortunately can result in a decrease of both the osteoconductivity and osteoinductivity of the bone material, which translates into a longer time for the bone material to incorporate properly into the host body or a complete rejection of the bone material.

In U.S. Pat. No. 5,725,579, issued to Fages et al, entitled "Process for Treating Bone Tissue and Corresponding Implantable Biomaterials," issued Mar. 10, 1998, it was disclosed that the degreasing step, step 110, and the rinse step, step 120, of the conventional method (FIG. 1) can be replaced by a single step of treating a bone material with supercritical fluid. However, under Fages, the remainder of the conventional method steps, namely, the steps 130, 140, 150, 160, and 170 (FIG. 1), must follow after treating the bone material with supercritical fluid, for the cleaning process to be completed.

SUMMARY OF THE DISCLOSURE

In accordance with the present invention, a method and apparatus for processing organic donor material is disclosed. In some embodiments of the present invention, a method of processing bone material using supercritical fluid comprises four steps. In the first step, the bone material is placed in a processing chamber. In the second step, supercritical degreasing is performed. In the third step, supercritical pulsing is performed. In the fourth step, a supercritical drying step is performed. The resulting bone material is both osteoinductive and osteoconductive, making it an ideal bone graft for implantation. All these steps are performed in situ in the processing chamber. The steps can be performed automatically, thus, dramatically reducing labor costs.

In some embodiments, a supercritical pulsing step, alone, presents useful improvements to the field of organic donor material processing. In other embodiments of the present invention, a supercritical drying step, alone, presents useful improvements to the field of organic donor material processing. In yet other embodiments, a step of exposing organic donor material to high energy radiation, such as gamma-ray radiation, is performed.

The present invention also includes a processing system for processing bone material using supercritical fluid. The processing system comprises a processing chamber, a vat, a pump, a heating element, a flow path, a tank, and a solvent port. The processing chamber houses the bone material to be processed. The vat is coupled to the processing chamber through a flow path. In operation of the system, a processing fluid flows through the flow path from the vat to the processing chamber. According to the preferred embodiment, once the processing fluid successfully enters the processing chamber, the processing fluid undergoes pressure pulsing and temperature pulsing with the help of the pump and the heating element, respectively. The processing fluid can thus fluctuate from its supercritical and nonsupercritical states based on the effects of the pulsing. Finally, the bone material is rinsed to dry it properly. The rinsing agent in the preferred embodiment is a mixture of $CO_2$ and alcohol, which is added to the processing chamber through the flow path. The alcohol enters the flow path from the tank through the solvent port. Optionally, gamma radiation can also be applied to the bone material.

DETAILED DESCRIPTION

The present invention discloses a method of and a system for processing organic donor material using supercritical fluids, such as supercritical $CO_2$. In the preferred embodiment of the present invention, the organic donor material is bone material. Supercritical fluids have surprisingly efficient extraction and cleaning capabilities, particularly with bone material. Supercritical fluids are superior to most chemicals used in the conventional bone material processing method, because supercritical fluids can infuse bone material like a gas and dissolve undesirable substances, such as fat, bacteria, and viruses, like a liquid. Furthermore, supercritical fluid extraction and processing can be controlled by adjusting certain variables, such as pressure and temperature, so that selected contaminants can be extracted, while leaving desired bone components (such as collagen and growth proteins) unharmed in the final matrix product of the material.

Figure 2A:
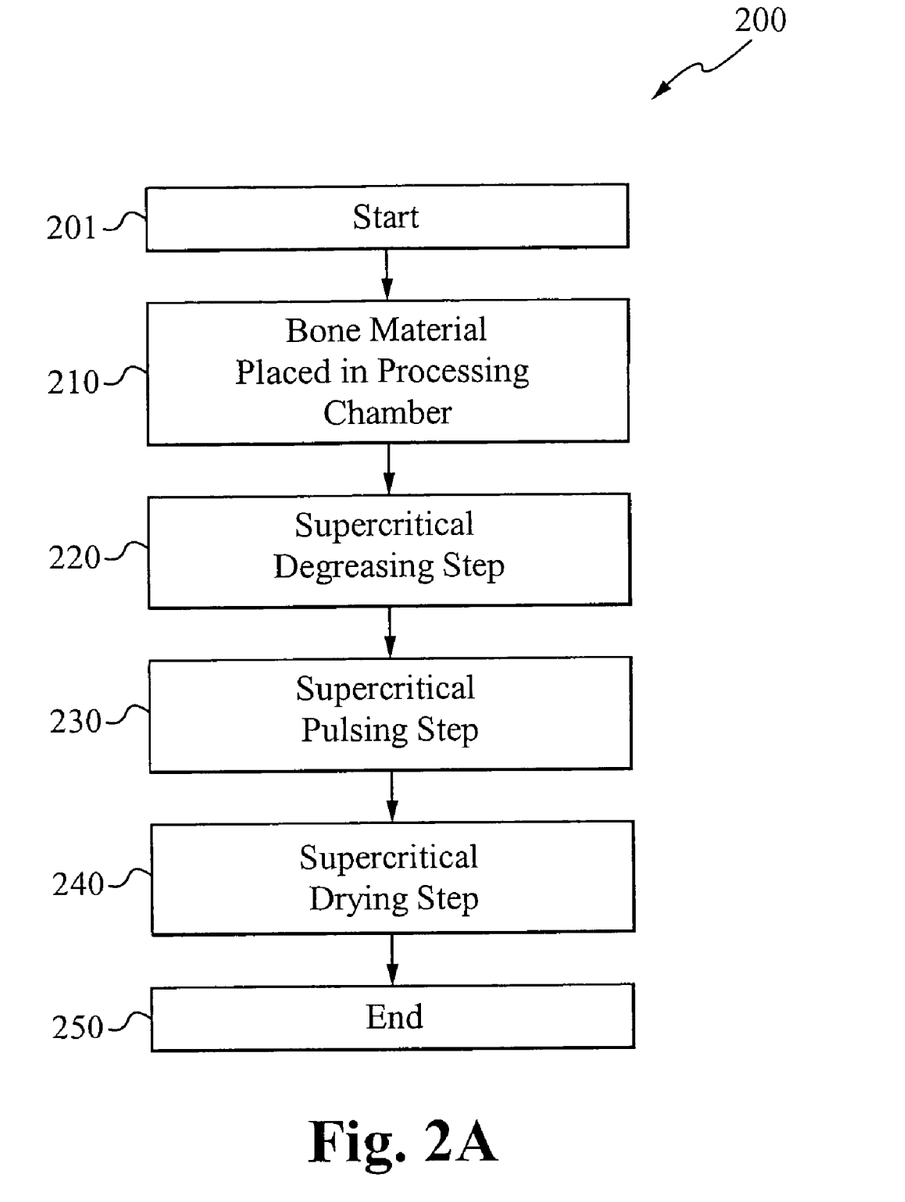
FIG. 2A is a flow chart illustrating a processing sequence of steps for processing bone material in accordance with a preferred embodiment of the present invention.

FIG. 2A illustrates a processing sequence 200 for processing organic donor material in accordance with the preferred embodiment of the invention. At the start step 201, bone material is provided. In some embodiments of the present invention autografts are provided. In other embodiments of the present invention, allografts, isografts, or xenografts are provided. In the preferred embodiment, the bone material is an allograft, from a human donor or a cadaver, intended for implantation into a human host. At the step 210, the bone material to be processed is placed in a processing chamber. In the preferred embodiment of the present invention, a single processing chamber is used throughout the processing sequence 200.

Next, a supercritical degreasing step 220 is performed. The degreasing step 220 involves delivering a supercritical fluid along with a degreasing chemistry to the processing chamber that holds the bone material. The degreasing chemistry aides in bone degreasing and in extracting liquids from the bone matrix. Preferably, the supercritical fluid is supercritical CO, and the degreasing chemistry is an alcohol, such as acetone. It is well known that $CO_2$ reaches its supercritical state when the temperature is above 30.5 degrees Centigrade and the pressure is above 1070.4 psi. The degreasing step 220 concludes with flushing the supercritical fluid and degreasing chemistry from the processing chamber.

Next, a supercritical pulsing step 230 is performed. The supercritical pulsing step involves delivering substantially pure supercritical fluid to the processing chamber and pulsating the fluid. Preferably, the supercritical fluid is supercritical $CO_2$. The pulsing of the supercritical fluid inside the processing chamber involves fluctuating the pressure of the supercritical fluid, fluctuating the temperature of the supercritical fluid, or a combination thereof. Pulsing the supercritical fluid is performed to kill and extract contaminants, such as bacteria, donor cells, viruses, and the like which are present within the bone material.

In some embodiments of the present invention, supercritical $CO_2$ fluctuates in a cycle from its supercritical state to its nonsupercritical state, through the varying ranges of pressure and temperature. Alternatively, pulsing can occur from a first supercritical pressure and a second supercritical pressure. However, it will be readily apparent to those having ordinary skill in the relevant art that a number of temperature and pressure fluctuations may be used to kill the contaminants present in the bone material.

The destruction of the contaminants occurs as the supercritical fluid infuses into the undesirable contaminants. Once infused into the contaminants, the step of pulsing pressure and temperature cause the membranes of the contaminants to explode or implode. In a preferred embodiment, the pulsing step is rapid, which in turn causes the supercritical fluid to disrupt, lyse and crack the walls of bacteria, viruses, donor cells, and the like. The supercritical pulsing step present clear advantages over the bacteria killing step practiced in the prior art because, unlike the use of an oxidizer to eliminate contaminants and a base chemistry to remove proteins, using a supercritical pulsing step eliminates unwanted contaminants, but does not destroy collagen, Bone Morphogenetic Proteins (BMPs), or other growth factors.

An additional benefit of the supercritical pulsing step 230 includes agitating contaminants present within the bone matrix, causing the contaminants to be removed from the bone matrix. In addition to killing contaminants, it is also beneficial to the osteoconductive and osteoinductive processes to remove dead contaminants from the bone matrix.

Another benefit of the supercritical pulsing step 230 lies in the ability of supercritical fluid to destroy prions. Prions are misshapen proteins typically found in fat that are thought to be linked with neurodegenerative diseases, such as mad cow disease, fatal familial insomnia, Gerstmann-Straussler syndrome, and Creutzfeldt-Jakob disease, to name a few. Prions are extremely difficult to kill, and under the conventional method (FIG. 1), strong oxidizers at the step 130 are used to accomplish this task. However, strong oxidizers in the conventional method can be advantageously replaced by supercritical fluids in the present invention, since supercritical fluids also eliminate prions. Thus, the use of supercritical fluid as an extractor of contaminants, including prions, at the step 230 (FIG. 2) in accordance with the present invention, prevents the transfer of diseases from the donor to the host via a bone transplant, without the disadvantage of using a multitude of strong, sometimes toxic chemicals.

The supercritical pulsing step 230 ends with flushing the fluid and the contaminants from the processing chamber. In some embodiments of the present invention a recirculation loop system is utilized to reuse supercritical fluid after the contaminants and the supercritical fluid exit the processing chamber. In some embodiments of the present invention, the contaminants are filtered out from the supercritical fluid using a filter, and the remaining supercritical fluid reenters the processing chamber through a loop, for the supercritical fluid to be reused for another next cycle.

In an alternative embodiment, the supercritical fluid enters the processing chamber through a flow path. Through pulsing, the supercritical fluid extracts the contaminants, which separate from bone material without a filter or a recirculation loop. For instance, contaminants can separate from bone material through condensation, preferably in one processing chamber. Those skilled in the art will also recognize other processes for separating contaminants from bone material, without using filtration or recirculation systems.

Next, at the step 240, the bone material is dried using supercritical fluid and a drying chemistry. In some embodiments of the present invention, a combination of supercritical $CO_2$ and alcohol is used for the proper rinsing of the bone material. In some embodiments of the present invention, acetone is used as the drying chemistry. The use of the supercritical drying step presents clear advantages over the prior art because using supercritical fluid for the delivery of the drying chemistry allows the drying agent to more-fully permeate the bone matrix to remove unwanted moisture. This step of drying is important due to the adverse effects of left over moisture with the bone matrix such as the prevention of cell migration through the structure (resulting in a decreased osteoconductivity) and the cracking of the bone structure as the bone material is cooled down to preserve the graft, among other negative effects. Finally, at the step 250, the bone material is ready to be implanted into the host's body.

Although the preferred embodiment of the present invention comprises a process including a supercritical degreasing step, a supercritical pulsing step and a supercritical drying step; it will be clear to those having ordinary skill in the art that the pulsing step, alone, presents useful improvements over the prior art. As explained, utilizing a process of pulsing a supercritical fluid to kill contaminants provides a clear improvement over the prior art in that the final product is the ideal bone graft material; that is, it is not only osteoinductive and osteoconductive (since its collagen and BMPs are still intact), but it is also clean of contaminants, such as viruses, bacteria, donor cells and the like.

Furthermore, it will be clear that the supercritical drying step also stands on its own and provides useful improvements over the prior art. Utilizing a supercritical fluid along with a drying agent allows the drying chemistry to more fully permeate the bone structure to remove unwanted moisture from the bone matrix.

Figure 2B:
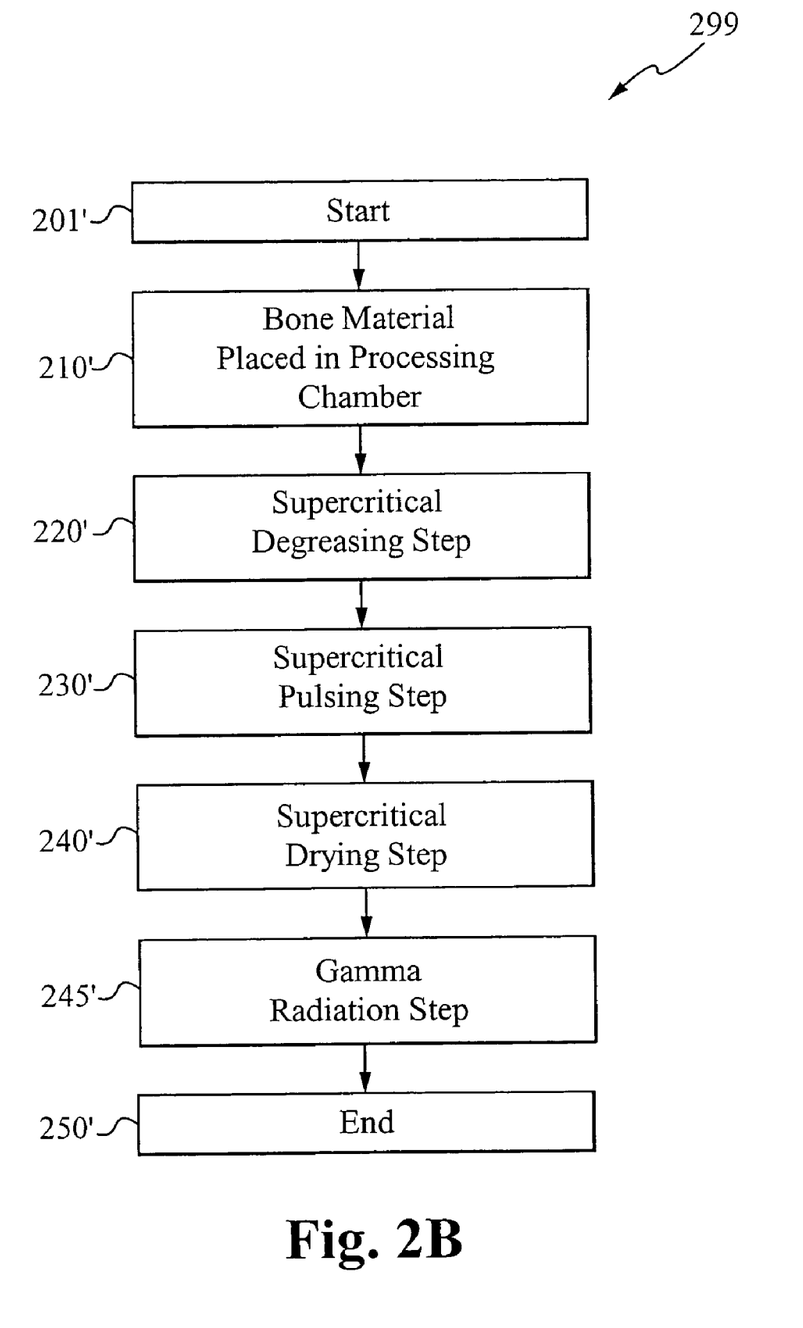
FIG. 2B is a flow chart illustrating a processing sequence of steps for processing bone material in accordance with an alternative embodiment of the present invention.

FIG. 2B illustrates an alternative processing sequence 299 for processing bone material in accordance with the preferred embodiment of the invention. The alternative processing sequence 299 is substantially similar to the processing sequence 200 with one additional step. Specifically, the alternative processing sequence involves: the start step 201' of obtaining bone material, a step 210' of placing bone material into a processing chamber, a supercritical degreasing step 220', a supercritical pulsing step 230', and a supercritical drying step 240'. Furthermore, after the supercritical drying step 240', a gamma radiation step 245' occurs as the bone material is bombarded with gamma radiation. At the step 250', the bone material is ready to be implanted into the host's body.

Figure 3A:
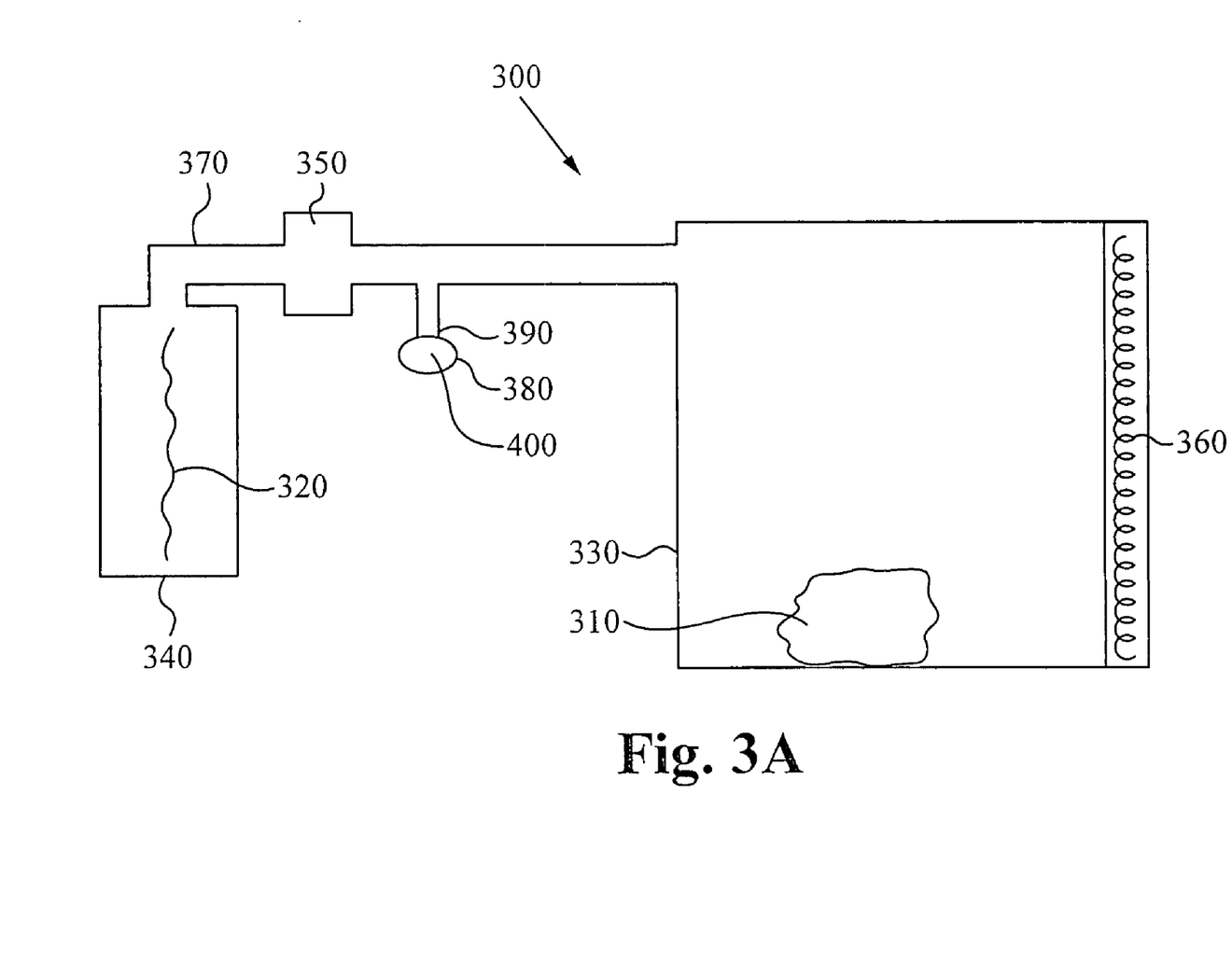
FIG. 3A is a block diagram illustrating a processing system for processing bone material in accordance with the preferred embodiment of the present invention.

FIG. 3A illustrates a processing system 300 for processing bone material 310 using a processing fluid 320, in accordance with some embodiments of the present invention. The processing system 300 comprises a processing chamber 330, a vat 340, a pump 350, a heating element 360, a flow path 370, a tank 380, and a solvent port 390. The processing chamber 330 is coupled to the vat 340 through the flow path 370. The pump 350 and the heating element 360 are coupled to the processing system 300. The tank 380 is coupled to the flow path 370 through a solvent port 390.

Initially, the processing chamber 330 houses the bone material 310 to be processed. In the preferred embodiment, the bone material 310 is an allograft from a human donor intended for a human host. While FIG. 3 illustrates a processing system 300 having a single processing chamber 330, it will be apparent to those skilled in the art that the processing system 300 can comprise any number of processing chambers for performing multiple processes on bone material or for concurrently processing multiple bone materials.

Processing fluid 320 is directed to the processing chamber 330 through the flow path 370. In some embodiments of the present invention an agent is added to the processing fluid 320 before entering the processing chamber. According to the preferred process 200, an agent 400 is added to a portion of processing fluid 320 from the tank 380 through the solvent port 390. In some embodiments of the present invention, the agent is a degreasing agent such as acetone, however, those having ordinary skill in the relevant art will appreciate that any degreasing agent is similarly applicable. The degreasing agent is mixed with the supercritical fluid 320 to form a degreasing chemistry. The degreasing chemistry is directed into the processing chamber 330 to achieve the supercritical degreasing step 220.

Also, according to the preferred process 200, the degreasing agent is flushed from the processing chamber 330 and the supercritical pulsing step 230 begins. According to this step, supercritical fluid 320 flows from the vat 340 through the flow path 370 and into the processing chamber 330. Once the processing fluid 320 successfully enters the processing chamber 330, the processing fluid 320 undergoes pulsing to begin the extraction of the contaminants contained on or within the bone material 310.

The term "pulsing" in reference to the processing system 300 refers to the fluctuation of the processing fluid 320, such as $CO_2$, between its nonsupercritical state and its supercritical state or from one supercritical pressure and another supercritical pressure. As a result of pulsing the processing fluid 320, undesirable contaminants are extracted. Pulsing can be done any number of ways. Preferably, pulsing can be accomplished by fluctuating the pressure of the processing fluid 320 with the help of the pump 350. Alternatively, temperature pulsing can be applied to the processing fluid 320 with the heating element 360. In yet another alternative embodiment, both pressure pulsing and temperature pulsing can be accomplished with the help of the pump 350 and alternatively the heating element 360, respectively.

In the preferred embodiment, the processing fluid 320 infuses into the undesirable contaminants and, if necessary, lyses those contaminants. Such contaminants include but are not limited to viruses, bacteria, donor cells, prions and the like.

Also, according to the preferred process 200, the supercritical fluid 320 used in the supercritical pulsing step 230 is flushed from the processing chamber 330 and bone material 310 is subjected to a supercritical drying step 240 to dry it properly. The drying agent in the preferred embodiment is a mixture of the processing fluid 320 and an alcohol. Preferably, the processing fluid 320 is $CO_2$. The processing fluid 320 flows from the vat 340 through the flow path 370 to the processing chamber 330. An agent 400, such as an alcohol, flows from a tank 380 through a solvent port 390 to the flow path 370. Once it reaches the flow path 370, the agent 400 mixes with the $CO_2$, and the mixture of the agent 400 and $CO_2$ finally reaches the processing chamber 330. It will be apparent to those skilled in the art that the rinsing agents can be any agents that cleanse the bone material 310 and leave it dry for proper implantation into the host.

In some embodiments, the agent 400 is the same agent used in the degreasing step. In the preferred embodiment, the agent 400 is acetone. In some embodiments, multiple agents are utilized and are delivered to the flow path 370 via multiple tanks (not shown) and solvent ports (not shown).

In some embodiments of the present invention, following the application of the rinsing agents, gamma radiation can also be applied to the bone material 310. After its processing through the processing system, the final product is a bone material that is both osteoinductive and osteoconductive, making it an ideal bone graft for implantation. Such an ideal bone graft translates to a shorter healing time for the host, fewer post-implant operations, shorter hospital stays, and less expense for the host.

It will be readily apparent to one skilled in the art that various modifications may be made to the embodiments without departing from the spirit and scope of the invention. For instance, a recirculation loop, additional chemistry vats, or the like can be optionally added to the processing system.

Figure 3B:
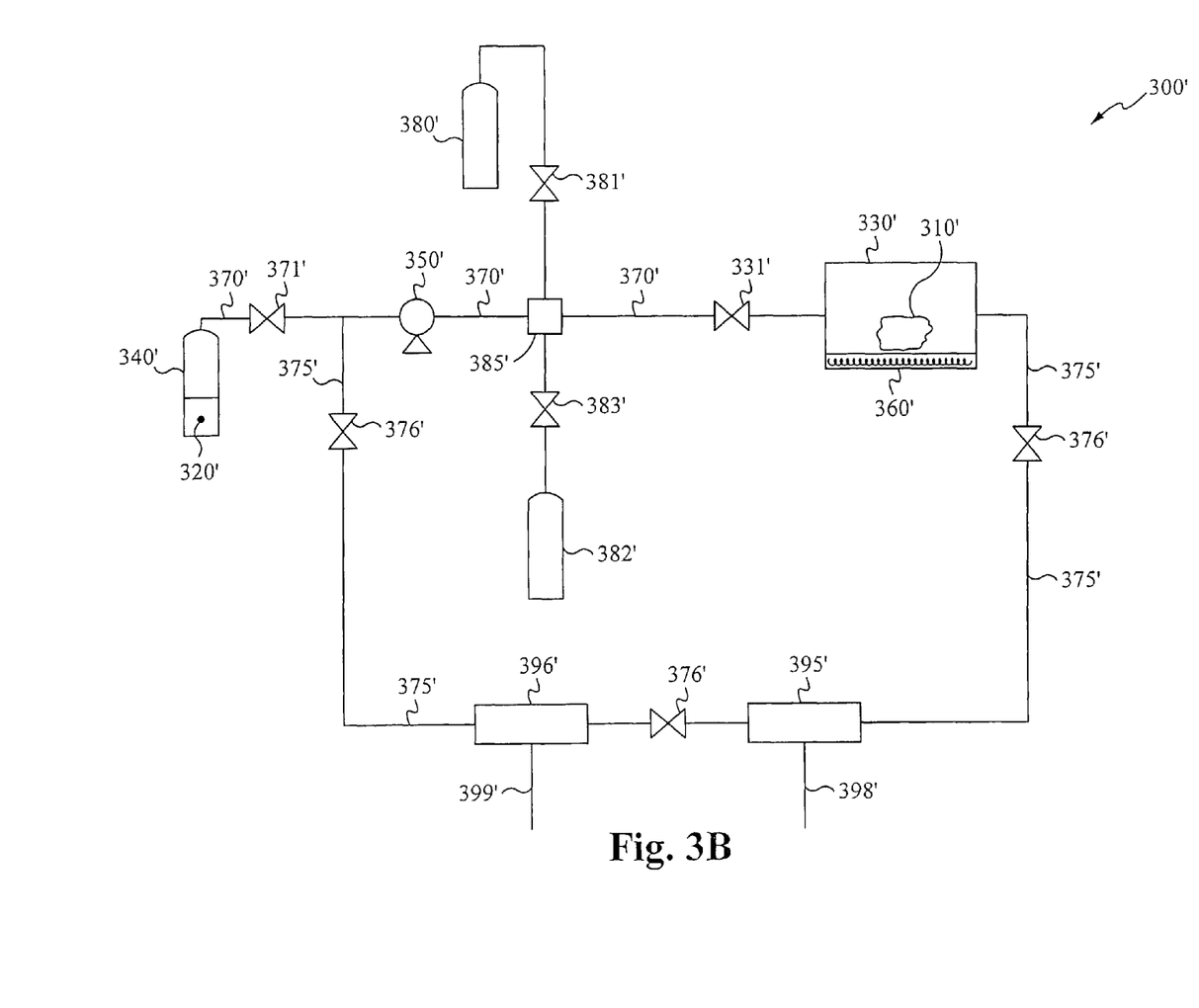
FIG. 3B is a block diagram illustrating an alternative processing system for processing bone material using a recirculation loop in accordance with the some embodiments of the present invention.

FIG. 3B illustrates a processing system 300' for processing bone material 310' using a processing fluid 320' in accordance with some embodiments of the present invention. The processing system 300' comprises a processing chamber 330', a vat 340', a pump 350', a flow path 370', a valve 371', a first chemistry tank 380', a second chemistry tank 382', a mixer 385', a recirculation loop 375', and components 395' and 396'.

As shown in FIG. 3B, the vat 340', the first chemistry tank 380' and the second chemistry tank 382' are coupled to the mixer 385'. A valve 381' is provided between the first chemistry tank 380' and the mixer 385' to optionally ensure that fluid delivered to the mixer 385' from the first chemistry tank 380' possesses some prerequisite pressure. Likewise, a valve 383' is provided between the second chemistry tank 382' and the mixer 385'. In some embodiments of the present invention, heaters (not shown) heat the chemistry contained within the chemistry tanks to heat the chemistries to some prerequisite temperature.

The mixer 385' is configured to receive and mix processing fluid 320' from the vat 340' and one or more chemistries from the first chemistry tank 380' and/or the second chemistry tank 382'. The mixed fluid is delivered via the flow path 370' to the processing chamber 330'. A valve 331' is positioned between the mixer 385' and the processing chamber 330' to optionally ensure that fluid delivered from the mixer 385' to the processing chamber 330' possesses some prerequisite pressure. In some embodiments of the present invention, the valve 331' is dynamically controllable to vary the pressure of the fluid delivered to the processing chamber in order to accomplish the pulsing step, as explained above. Likewise, a heating element 360' is coupled to the processing chamber 330' and the heating element 360' is dynamically controllable to vary the temperature of the fluid delivered to the processing chamber in order to accomplish the pulsing step, as explained above.

According to FIG. 3B, the fluid in the processing chamber 330' exits the processing chamber 330' into a recirculation loop 375'. A number of valves 376' are positioned within the recirculation loop 375' to control pressure. Also contained within the recirculation loop 375' are components 395' and 396'. Components 395' and 396' can include, but are not limited to separator, filters or the like. In some embodiments of the present invention, outlet lines 398' and 399' are coupled to the components 395' and 396', respectively.

In some embodiments of the present invention, contaminants are filtered out from the processing fluid, leaving remaining fluid. The recirculation loop 375' is configured such that the remaining fluid reenters the flow path 370' to be reused for the next processing cycle. Any number of cycles and types of filters necessary to extract undesirable contaminants of bone material can be used, based on the application at hand.

Reference has been made in detail to the preferred and alternative embodiments of the invention, examples of which are illustrated in the accompanying drawings. While the invention has been described in conjunction with the preferred embodiments, it will be understood that they are not intended to limit the invention to these embodiments. On the contrary, the invention is intended to cover alternatives, modifications and equivalents, which may be included within the spirit and scope of the invention. Furthermore, in the detailed description of the present invention, numerous specific details have been set forth in order to provide a thorough understanding of the present invention. However, it should be noted that the present invention may be practiced without these specific details. In other instances, well known methods, procedures and components have not been described in detail as not to unnecessarily obscure aspects of the present invention.

What is claimed is:

1. A method of processing organic donor material for grafting while avoiding elimination of growth factors, the method comprising:
   a. providing organic donor material within a processing chamber, wherein the organic donor material contains contaminants;
   b. introducing only a fluid and an alcohol into the processing chamber; and
   c. performing a pulsing step on the fluid, wherein the pulsing step kills substantially all the contaminants present within the organic donor material while avoiding elimination of growth factors.

2. The method of claim 1, wherein the fluid is introduced to the processing chamber in a supercritical state.

3. The method of claim 2, wherein the pulsing step comprises:
   a. fluctuating the pressure of the fluid, causing the contaminants to implode.

4. The method of claim 2, wherein the pulsing step comprises:
   a. allowing at least a portion of the fluid in its supercritical state to penetrate into the contaminants;
   b. fluctuating the pressure of the fluid causing the portion of the fluid penetrated into the contaminants to explode the contaminants.

5. The method of claim 2, wherein the pulsing step comprises:
   a. fluctuating the temperature of the fluid in its supercritical state, thereby killing the contaminants.
6. The method of claim 2, wherein the pulsing step comprises:
   a. fluctuating the temperature and pressure of the fluid, thereby killing the contaminants.
7. The method of claim 2, wherein the pulsing step comprises:
   a. fluctuating the fluid between a first supercritical pressure and a second supercritical pressure, thereby killing the contaminants.
8. The method of claim 1, wherein the fluid is supercritical $CO_2$.
9. The method of claim 1, wherein the organic donor material is bone harvested from a human donor.
10. The method of claim 1, wherein the organic donor material is bone harvested from an animal donor.
11. The method of claim 1, wherein the alcohol is acetone.
12. The method of claim 1, wherein the pulsing step agitates the contaminants present in the organic donor material, thereby removing the contaminants from the organic donor material.
13. The method of claim 1, further comprising:
   a. exposing the organic donor material to gamma-ray radiation.
14. An apparatus for processing organic donor material for grafting while avoiding elimination of growth factors, the apparatus comprising:
   a. a processing chamber, wherein the processing chamber is configured to hold an organic donor material contining contaminants;
   b. a supply of a fluid is configured to contain only the fluid and an alcohol;
   c. a means for bringing the fluid to a supercritical state, forming a supercritical fluid;
   d. a means for introducing the supercritical fluid into the processing chamber; and
   e. a means for pulsing the supercritical fluid within the processing chamber, thereby removing contaminants from organic donor material while avoiding elimination of growth factors.
15. The apparatus of claim 14, wherein the supercritical fluid is supercritical $CO_2$.
16. The apparatus of claim 14, wherein the alcohol is acetone.
17. The apparatus of claim 14, further comprising:
   a. a means for exposing the organic donor material to gamma ray radiation.
18. A method of processing organic donor material for grafting while avoiding elimination of growth factors, the method comprising:
   a. providing organic donor material within a processing chamber, wherein the organic donor material contains contaminants;
   b. introducing a degreasing chemistry into the processing chamber, wherein the degreasing chemistry comprises a supercritical $CO_2$ and an alcohol only;
   c. introducing supercritical $CO_2$ into the processing chamber;
   d. performing a pulsing step on the supercritical $CO_2$, wherein the pulsing step kills substantially all the contaminants present within the organic donor material while avoiding elimination of growth factors; and
   e. introducing a drying chemistry into the processing chamber, wherein the drying chemistry comprises supercritical $CO_2$ and acetone only.
19. The method of claim 18, further comprising:
   a. exposing the organic donor material to gamma-ray radiation.

* * * * *

UNITED STATES PATENT AND TRADEMARK OFFICE
CERTIFICATE OF CORRECTION

| | | |
|---|---|---|
| PATENT NO. | : 8,007,718 B1 | Page 1 of 1 |
| APPLICATION NO. | : 12/151840 | |
| DATED | : August 30, 2011 | |
| INVENTOR(S) | : Biberger | |

It is certified that error appears in the above-identified patent and that said Letters Patent is hereby corrected as shown below:

<u>In the Specification</u>
At column 4, line 12, please replace "CO," with -- $CO_2$, --.

Signed and Sealed this
Eleventh Day of October, 2011

David J. Kappos
*Director of the United States Patent and Trademark Office*